United States Patent [19]

Grabiak et al.

[11] Patent Number: 4,851,131

[45] Date of Patent: Jul. 25, 1989

[54] PROCESS FOR TREATING GLYPHOSATE PROCESS WASTE STREAMS

[75] Inventors: Raymond C. Grabiak; Dennis P. Riley, both of St. Louis, Mo.

[73] Assignee: Monsanto Company, St. Louis, Mo.

[21] Appl. No.: 139,995

[22] Filed: Dec. 31, 1987

[51] Int. Cl.$^4$ .............................................. C02F 1/74
[52] U.S. Cl. ..................................... 210/763; 210/908
[58] Field of Search ............... 210/757, 762, 763, 908; 260/502.5 R, 502.5 F

[56] References Cited

U.S. PATENT DOCUMENTS 3,442,802  5/1969  Hamilton et al. .................. 210/763
3,487,016  12/1969  Zeff .................................... 210/763
4,454,043  6/1984  Ting et al. .......................... 210/659

FOREIGN PATENT DOCUMENTS 2425587  12/1974  Fed. Rep. of Germany ...... 210/762

Primary Examiner—Peter Hruskoci
Attorney, Agent, or Firm—Linda L. Lewis; Frank D. Shearin

[57] ABSTRACT

Waste streams from N-phosphonomethylglycine facilities are treated to remove by-products and unreacted raw materials by heating the waste stream in the presence of a transition metal catalyst and contacting the waste stream with an oxygen-containing gas.

8 Claims, No Drawings

PROCESS FOR TREATING GLYPHOSATE PROCESS WASTE STREAMS

BACKGROUND OF THE INVENTION

This invention relates to a process for treating waste streams from a N-phosphonomethylglycine facility, and more particularly, relates to a method for treating such waste streams using formaldehyde and oxygen with a transition metal catalyst.

N-phosphonomethylglycine, known in the agricultural chemical art as glyphosate, is a highly effective and commercially important phytotoxicant useful in controlling the growth of germinating seeds, emerging seedlings, maturing and established woody and herbaceous vegetation, and aquatic plants. N-phosphonomethylglycine and salts thereof are conveniently applied in the form of an aqueous solution as a postemergent phytotoxicant or herbicide for the control of one or more monocotyledonous species and one or more dicotyledonous species. Moreover, such compounds are characterized by broad spectrum activity, i.e., they control the growth of a wide variety of plants, including but not limited to ferns, conifers, aquatic monocotyledons, and dicotyledons.

SUMMARY OF RELATED ART

Numerous patents described processes for the preparation of N-phosphonomethylglycine. Hershman, U.S. Pat. No. 3,969,398, describes a process for preparing N-phosphonomethylglycine by the oxidation of N-phosphonoiminodiacetic acid.

Gaertner, Canadian Pat. No. 1,039,739, describes a process for producing N-phosphonomethylglycine by reacting aminomethylphosphonic acid and esters with glyoxal or glyoxylic acid to form a carbonylaldiminomethanephosphonate. Thereafter, the carbonylaldiminomethanephosphonate is subjected to catalytic hydrogenation to reduce the double bond and produce N-phosphonomethylglycine or its esters. The ester groups are then hydrolyzed to produce N-phosphonomethylglycine.

Franz, U.S. Pat. No. 3,799,758, describes the preparation of N-phosphonomethylglycine by reaction of ethyl glycinate formaldehyde, and diethyl phosphite. Alternative processes described by Franz include phosphonomethylation of glycine with chloromethylphosphonic acid in the presence of sodium hydroxide and oxidation of N-phosphinomethylglycine with mercuric chloride.

Gaertner, U.S. Pat. No. 3,927,080, describes the production of N-phosphonomethylglycine by acid-catalyzed dealkylation of N-t-butyl-N-phosphonomethylglycine or its esters. Tertiary butylamine is reacted with a bromoacetate ester to produce an ester of N-t-butylglycine which is in turn reacted with formaldehyde and phosphorous acid to produce the N-t-butyl-N-phosphonomethylglycine precursor.

Ehrat, U.S. Pat. No. 4,237,065, describes a process in which glycine is condensed with formaldehyde in the presence of a tertiary base to produce an N-methylglycine, which is in turn reacted with phosphorous acid to produce N-phosphonomethylglycine.

Pfliegle et al, U.S. Pat. No., 4,065,491, discloses a process in which N-phosphonomethylglycine is prepared by condensation of glycine, formaldehyde, and a dialkyl phosphite in an aqueous alkaline medium to form an N-phosphonomethylglycine dialkyl ester. The latter is hydrolyzed with a mineral acid to produce N-phosphonomethylglycine.

All of these processes produce waste streams containing certain by-products as a result of undesired side reactions and unreacted materials. The term waste stream as used herein is the reaction mixture resulting from the manufacture of N-phosphonomethylglycine after removal of a substantial portion of that product. The specific composition of the waste stream will of course depend on the particular process and conditions used in the manufacture. Examples of such by-products and unreacted materials include formaldehyde, carbon dioxide, N-substituted N-phosphonomethylglycine, N-substituted and N-unsubstituted aminoethylphosphonic acid, as well as unrecovered N-phosphonomethylglycine. From time to time it becomes necessary to remove these materials from the process to prevent contamination of the desired N-phosphonomethylglycine.

Various means have been considered for disposing of the waste stream from the process to manufacture N-phosphonomethylglycine. For example, the waste stream from the glyphosate process can be diluted with other process waste streams and treated in an aerobic biosystem to meet aqueous effluent limits established by the various regulatory agencies. Alternatively, the waste stream can be segregated from other waste streams and incinerated at high temperatures to destroy these unwanted chemicals. Other methods have been considered such as reaction with various chemicals at high temperatures and/or high pressures to destroy these products.

Although the procedures described above, as well as others that might be considered by those skilled in the art, reduce the levels of the N-phosphonomethylglycine and accompanying by-products from the manufacturing process in the waste stream to lower levels, these waste treatment procedures have some disadvantages such as high operating costs, high capital costs, limited destruction efficiency or other environmental concerns.

The process disclosed and claimed herein is a treatment process for these waste streams which is simple and cost effective procedure for reducing the concentration of N-phosphonomethylglycine and related derivatives to an acceptable level for direct discharge, to an aerobic biosystem before discharge. The present process overcomes the intrinsic problems associated with waste treatment procedures heretofore considered.

SUMMARY OF THE INVENTION

The present invention is directed to a process for treating waste streams from an N-phosphonomethylglycine process which comprises heating the waste streams in the presence of a transition metal catalyst and contacting the hot waste stream containing the transition metal catalyst with an oxygen-containing gas, e.g. a gas containing free oxygen. Optionally, a stoichiometric excess of formaldehyde to the waste products can be added with the transition metal catalyst to enhance the overall efficiency of the waste treatment process.

It is known in the art that N-phosphonomethylglycine can be produced by oxidizing N-phosphonomethyliminodiacetic acid using various oxidizing methods. U.S. Pat. No. 3,950,402 discloses a method wherein N-phosphonomethyliminodiacetic acid is oxidized to N-phosphonomethylglycine in aqueous media using a free oxygen-containing gas and a heterogeneous noble metal-based catalyst such as palladium, platinum or rhodium. U.S. Pat. No. 3,954,848 discloses the oxidation of N-phosphonomethyliminodiacetic acid with hydrogen peroxide and an acid such as sulfuric or acetic acid. Hungarian Patent Application No. 011706 discloses the oxidation of N-phosphonomethyliminodiacetic acid with peroxide in the presence of metals or metal compounds.

R. J. Motekaitis, et al., Can. J. Chem., 58, 1999 (1980) disclose the iron(III) or copper(II) catalysed oxidative dealkylation of ethylene diaminetetracetic acid (EDTA) and nitrilotriacetic acid (NTA), both of which have iminodiacetic acid groups, R. J. Moteakitis, et al, Can. J. Chem., 60, 1207 (1982) disclose that certain metal ions, such as Ca(II), Mg(II), Fe(II), Zn(II) and Ni(II) chelate with EDTA and stabilize against oxidation, thereby reducing the rate of oxidative dealkylation.

None of the above references discloses the use of transition metal catalysts to treat glyphosate process waste streams.

DETAILED DESCRIPTION OF THE INVENTION

The process of this invention involves contacting a waste stream from a N-phosphonomethyliminodiacetic acid process with a transition metal catalyst in a mixture or solution. This mixture or solution is contacted with a molecular oxygen-containing gas while heating the reaction mass to a temperature sufficiently elevated to initiate and sustain the oxidation reactions of N-substituted-N-phosphonomethylglycine derivatives. Optionally, the reaction mixture or solution may contain a stoichiometric excess of formaldehyde to accelerate the oxidation rates by methylation.

The transition metal catalyst suitable for use in the present invention can be any one or more of several transition metal compounds such as manganese, cobalt, iron, nickel, chromium, ruthenium, aluminum, molybdenum, vanadium, copper, zinc and cerium. The catalyst can be in the form of salts such as manganese salts, e.g., manganese acetate, manganese chloride, manganese sulfate; complexes such as manganese(II)bis-(acetylacetonate) $(Mn(II)(acac)_2)$; cobalt salts such as Co(II)$(SO_4)$, Co(II)(acetylacetonate), $CoCl_2$, $CoBr_2$, Co(-$NO_3)_2$ and cobalt acetate; cerium salts such as $(NH_4)_4Ce(SO_4)$ and $(HN_4)_2Ce(NO_3)_6$, iron salts such as $FeCl_3$, $(NH_4)_2Fe(SO_4)_2$, iron (III)(dicyano)-(bisphenanthroline)$_2$(tetrafluoro)borate salt and $K_3Fe(CN)_6$, and other metal salts such as $NiBr_2$, $CrCl_3$, $(RuCl_2(Me_2SO)$, $RuBr_3$, $Al(NO_3)_3$, $K_4Mo(CN)_8$, $VO(acetylacetonate)_2$ and $VOSO_4$. A preferred manganese catalyst is a Mn(II) salt. A preferred cobalt catalyst is a Co(II) salt such as Co(II)$(SO_4)$, Co(II)$Cl_2$, Co(II)$Br_2$, Co(II)$(OH)_2$ and Co(II)acetate.

The concentration of the transition metal catalyst in the reaction solution can vary widely preferably in the range of about 0.5M to 0.0001M metal ion concentration in the waste stream. If high catalyst concentrations are used, the oxidation reactions are accelerated.

The waste stream from the N-phosphonomethylglycine manufacture as described above is adjusted to about pH 1 to about pH 10, preferably to about pH 6 to about pH 9. The pH of the waste stream can be adjusted by well known methods, such as adding an alkali metal hydroxide, alkali metal carbonate or an alkaline earth hydroxide. Alkali metal hydroxides are preferred, such as sodium hydroxide or potassium hydroxide. Calcium hydroxide is also preferred because of its cost and effectiveness. Thereafter, a solution or slurry of catalyst in water is added to the waste stream. As indicated earlier, a stoichiometric excess of formaldehyde or paraformaldehyde can be added to the waste stream.

The waste stream is then placed in a suitable container, pressurized and heated. An excess of an oxygen-containing gas is continuously introduced with agitation under pressure. The oxygen-containing gas is a molecular oxygen-containing gas. The molecular oxygen can be admixed with any number of inert gases, such as helium, neon, argon, nitrogen and the like. Air can be used in the process of the present invention, but because of the large volume of inert nitrogen, it is preferred to use an oxygen-containing gas containing at least 50 percent by volume oxygen, preferably at least 75 percent by volume oxygen, such as oxygen enriched air, and most preferably to use substantially pure oxygen $(99+\%O_2)$. Under these conditions, most of the N-substituted N-phosphonomethylglycine is oxidized to either N-phosphonomethylglycine, N-substituted-aminomethylphosphonic acid or phosphate, with the co-generation of formic acid and carbon dioxide. N-phosphonomethyl glycine is methylated and further oxidized to N-substituted-N-aminomethylphosphonic acids are also methylated in the presence of formaldehyde and further oxidized under the reaction conditions. The reaction is continued until virtually all of the non-N-phosphonomethylglycine in the mixture has been destroyed. Thereafter, the batch is cooled, and transferred to an appropriate area for disposal.

The effluent stream from the claimed process described above contains only trace levels of N-phosphonomethylglycine and N-substituted derivatives. The major chemical products of this treatment process are formic acid, carbon dioxide, aminomethylphosphonic acid and methylated derivatives, and phosphoric acid. The overall destruction of residual N-phosphonomethylglycine and its derivatives using this process is greater than about 85% within six hours or less.

The pressure and temperature at which the waste stream is contacted with the oxygen-containing gas is only limited by the available equipment and safety considerations. Contacting the waste stream at ambient temperature and pressure with air does not provide satisfactory results. The waste stream should be contacted with the oxygen-containing gas at a pressure of from $1 \times 10^5$ Pascals (14.5 psig) to $20 \times 10^5$ Pascals (290 psig) and at a temperature below boil, for convenience. Preferably the pressure is at least $3.8 \times 10^5$ Pascals (55 psig) and the temperature is about 100° C. More preferably, the pressure is at least $4.5 \times 10^5$ Pascals (65 psig) and the temperature is about 120° C. Higher pressures and temperatures increase the reaction rate.

The transition metal catalyst is conveniently added to the waste stream by any convenient manner, such as a solid, solution or slurry.

The invention is further illustrated by, but not limited to, the following examples, where all percentages are by weight unless otherwise indicated.

EXAMPLE 1

Example illustrates the use of a manganese transition metal catalyst in the present invention with and without formaldehyde. A waste stream from a glyphosate process was obtained which contained by HPLC analysis 2.9% N-phosphonomethylglycine (GLY), 6.3% N-methyl-N-phosphonomethylglycine (NMG), 2.1% N- phosphonomethyliminodiacetic acid (GI) and 0.2% N-formylphosphonomethylglycine (NFG) and other minor impurities in water. The waste stream (66.5 g) was diluted with water (66.5 g) and neutralized with 17 g of 50 wt. % sodium hydroxide solution to pH 7.5. A series of runs was made wherein the amount of $MnCl_2$ $4H_2O$ (in 5 ml $H_2O$) and the amount of formalin was varied. The mixture of reactants was placed in a 300 ml stainless steel autoclave. The sealed autoclave was pressurized to 50 psig (343 kPa) with nitrogen and heated to 1120° C. with stirring (17 Hz). Upon attaining a temperature of 120° C., oxygen was sparged through the reaction mixture at a rate of 40 ml/min, while simultaneously venting the autoclave offgases to maintain a pressure of 50 psig (343 kPa). At the indicated reaction time, the oxygen flow was discontinued and the contents of the autoclave were allowed to cool to about 25° C. The percent destruction of the key components in the waste stream was determined by HPLC and are shown in Table 1 below.

The results summarized in Table I indicate that the manganese catalyzed treatment is effective in the destruction of GLY, NMG and GI. The presence of formalin increase the destruction of GLY in approximately equivalent reaction times (see examples 3 and 4).

TABLE I

| | Manganese-Catalyzed Treatment | | | | | |
|---|---|---|---|---|---|---|
| Run No. | $MnCl_2.4H_2O$ (g) | Formalin (g) | Reaction Time (min) | % Destruction | | |
| | | | | GLY | NMG | GI |
| 1 | 0.42 | 0.0 | 1080 | 88.9 | 97.7 | 100 |
| 2 | 0.05 | 0.0 | 250 | 67.0 | 96.0 | 100 |
| 3 | 0.05 | 0.0 | 245 | 75.0 | 98.0 | 100 |
| 4 | 0.14 | 12.5 | 240 | 99.2 | 98.3 | 98.3 |
| 5 | 0.05 | 12.5 | 246 | 99.2 | 97.7 | 97.5 |

EXAMPLE 2

Example 2 illustrates the use of a manganese transition metal catalyst in the present invention with and without formaldehyde. A waste stream from a glyphosate process was obtained which contained by HPLC analysis 1.7% GLY 3.2% NMG, 1.0% GI, 0.1% NFG and other minor impurities. The waste stream (125g) was neutralized with 17 g of 50% aqueous sodium hydroxide to a pH of 7.5. A series of runs was made wherein the amount of $MnCl_2.4H_2O$ (in 5 ml water) and the amount of formalin was varied. The mixture was placed in a 300 ml stainless steel autoclave. The autoclave was sealed and pressurized to 50 psig (343 kPa) with nitrogen and heated to 120° C. with stirring (17 Hz). A series of runs was made wherein the amount of $MnCl_2$ $4H_2$) (in 5 ml water) and the amount of formalin was varied. When the desired temperature was reached, the reaction mixture was sparged with oxygen gas at a rate of 40 ml/min. The autoclave offgases were vented while maintaining an autoclave pressure of 50 psig (343 kPa). At the indicated reaction time, the oxygen flow was discontinued and the contents of the autoclave allowed to cool to ambient temperature (about 25° C.). The percent destruction of the components in the waste stream were determined by HPLC and are shown in Table II below.

The results summarized in Table II indicate that the manganese catalyzed treatment is effective in destroying GLY, NMG and GI. The presence of formalin increases the destruction rate of GLY. (See examples 7 and 8).

TABLE II

| | Manganese-Catalyzed Treatment | | | | | |
|---|---|---|---|---|---|---|
| Run No. | $MnCl_2.4H_2O$ (g) | Formalin (g) | Reaction Time (min) | % Destruction | | |
| | | | | GLY | NMG | GI |
| 6 | 0.42 | 0.0 | 960 | 87.6 | 95.0 | 99.6 |
| 7 | 0.05 | 0.0 | 960 | 93.0 | 96.2 | 99.9 |
| 8 | 0.14 | 12.5 | 225 | 97.0 | 93.0 | 99.0 |

EXAMPLE 3

Example 3 illustrates the use of cobalt catalyst without formaldehyde in the present invention. The reactions were conducted in a modified Fisher-Porter glass pressure apparatus or an Engineer Autoclave 300 ml pressure reactor in which a stirrer was installed in the head, along with a sample port, a gas inlet, and a purged gas outlet. The stirrer maintained sufficient agitation to afford thorough gas-liquid mixing. The temperature was controlled at 100° C. by immersing the reactor in a constant temperature oil bath. A 0.5 M solution of the $CoCl_2$ transition metal catalyst was prepared with distilled, deionized water containing 0.5 M GI. The reactor was sealed and heated to 100° C., then pressurized to the 100 psig (686 kPa) with oxygen gas. Agitation was initiated. The run time was 18 h. The pH of the solution was adjusted with sodium hydroxide or sulfuric acid solution. A series of runs was made wherein the pH of the reaction was varied. The percent destruction of the GI and GLY combined were determined by HPLC and are shown in Table 3.

The results summarized in Table III indicate that the cobalt catalyst treatment is effective in destroying GLY and CI. The greatest destruction occurs at pH 4.00 (Example 11).

TABLE III

| Cobalt-Catalyzed Treatment | | |
|---|---|---|
| Run No. | pH | % Destruction GLY and GI combined |
| 9 | 1.80 | 72 |
| 10 | 2.25 | 84 |
| 11 | 4.00 | 100 |
| 12 | 1.09 | 65 |
| 13 | 0.77 | 90 |
| 14 | 1.7 | 83 |

EXAMPLE 4

Example 4 illustrates the use of iron catalyst without formaldehyde in the present invention. The reaction conditions were the same as those of Example 3, except that the catalyst concentration of $K_3Fe(CN)_6$ was 0.01 M, the run-time was 18 h. and the initial pH was 10.0. The percent destruction of the GI and GLY combined was determined by HPLC and found to be about 50%.

Although the invention has been described in terms of specified embodiments and operating techniques which are set forth in considerable detail, it should be understood that this is by way of illustration only, and that alternative embodiments and operating techniques will become apparent to those skilled in the art in view of the disclosure. For example, the process of the present invention could be useful to treat waste streams from other processes that make organophosphorus compounds, such as those disclosed in U.S. Pat. No. 3,288,846 for the preparation of aminoalkylenephosphonic acids useful as chelants. Accordingly, modifications can be made without departing from the spirit of the described invention.

We claim:

1. An oxidation process for treating waste streams containing N-phosphonomethylglycine and N-substituted derivatives thereof from a process for the manufacture of N-phosphonomethylglycine comprising:

A. adding formaldehyde to the waste stream in stoichiometric excess to the N-phosphonomethylglycine and N-substituted derivatives thereof in the waste stream;

B. heating the waste stream containing N-phosphonomethylglycine and by-products from the manufacture at a temperature sufficiently elevated to initiate and sustain the oxidation of said N-phonosphonomethylglycine and by-products; and C. contacting the waste stream with an excess of oxygen-containing gas required to oxidize N-phosphonomethylglycine and the by-products in the presence of an effective amount of a catalyst selected from the group consisting of the salts of manganese, cobalt, iron, nickel, chromium, ruthenium, aluminum, molybdenum, vanadian, copper, zinc and cerium to oxidize said N-phosphonomethylglycine and by-products.

2. A process of claim 1 wherein the catalyst is present in the amount of at least 0.0001 molar metal ion concentration in the waste stream.

3. A process of claim 1 wherein the waste stream is contacted with an oxygen-containing gas at a pressure of at least $1 \times 10^5$ Pascals and at a temperature below the boiling point of the waste stream.

4. A process of claim 3 wherein the waste stream is contacted with an oxygen-containing gas at a pressure of at least $3.8 \times 10^5$ Pascals.

5. A process of claim 3 wherein the waste stream is contacted with an oxygen-containing gas at a pressure of at least $4.5 \times 10^5$ Pascals.

6. A process of claim 3 wherein the pH of the waste stream is adjusted to between about pH 6 and about pH 9.

7. A process of claim 6 wherein the waste stream is contacted with an oxygen-containing gas containing at least 50% by volume oxygen.

8. A process of claim 7 wherein the catalyst is selected from the salts of manganese and cobalt.

* * * * *